(12) United States Patent
Bruggemann et al.

(10) Patent No.: US 8,512,285 B2
(45) Date of Patent: Aug. 20, 2013

(54) LATCHING AND CONTROL UNIT FOR INTEGRATION IN A MEDICAL DEVICE

(75) Inventors: Ulrich Bruggemann, Bridgewater, NJ (US); Christopher Jones, Tewkesbury (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/392,778

(22) PCT Filed: Sep. 15, 2010

(86) PCT No.: PCT/EP2010/063515
§ 371 (c)(1), (2), (4) Date: Jul. 10, 2012

(87) PCT Pub. No.: WO2011/032961
PCT Pub. Date: Mar. 24, 2011

(65) Prior Publication Data
US 2012/0271233 A1    Oct. 25, 2012

(30) Foreign Application Priority Data
Sep. 18, 2009  (EP) ................................ 09170719

(51) Int. Cl.
*A61M 37/00*  (2006.01)

(52) U.S. Cl.
USPC ........................................... 604/131

(58) Field of Classification Search
USPC ........................................... 604/131
See application file for complete search history.

(56) References Cited

U.S. PATENT DOCUMENTS

| 7,764,370 | B2 * | 7/2010 | Williams et al. | ............... 356/246 |
| 2003/0161744 | A1 | 8/2003 | Vilks et al. | |
| 2004/0108339 | A1 | 6/2004 | Hansen et al. | |
| 2007/0248477 | A1 * | 10/2007 | Nazarifar et al. | .......... 417/477.2 |

FOREIGN PATENT DOCUMENTS

| EP | 1839689 A1 | 10/2007 |
| WO | 9710864 A1 | 3/1997 |

OTHER PUBLICATIONS

Form PCT/IB/326, Notification Concerning Transmittal of International Preliminary Report on Patentability.

* cited by examiner

*Primary Examiner* — Aarti B Berdichevsky
(74) *Attorney, Agent, or Firm* — McDonnell Boehnen Hulbert & Berghoff LLP

(57) ABSTRACT

Latching and control unit for integration in a medical device for infusion of a medicament or removal of a substance of a human body by a drive means, the latching and control unit being adapted for controlling the movement of at least a first and a second movable component, the latching and control unit including a drive train, a detection device, coupling means, and a control device.

12 Claims, 4 Drawing Sheets

LATCHING AND CONTROL UNIT FOR INTEGRATION IN A MEDICAL DEVICE

The invention is related to a latching and control unit for integration in a medical device for infusion of a medicament or removal of a substance of a human body by a drive means.

WO 1997/010864 A1 provides a cartridge holder assembly designed to engage with and disengage from the pen body assembly and a lead screw retained against rotation when the selected dose is dispensed. The cartridge holder assembly has a plurality of internal splines for engaging the piston rod to the driving means when the pen body is fully threaded onto the cartridge holder assembly. Whilst this device provides a solution for the reset of a medication delivery pen drive mechanism it does require the user to align the cartridge holder with slots at the distal end of the piston rod which may be difficult for users with impaired eyesight and/or impaired dexterity.

An object of the invention is to provide a latching and control unit for latching a component of a medical device which allows a safe operation dependent of functional components of the medical device.

This object is solved by the features of claim 1. Further embodiments are descried in the subclaims referred back thereto.

According to the invention, a latching and control unit for integration in a medical device for infusion of a medicament or removal of a substance of a human body by a drive means is provided, the latching and control unit being adapted for controlling the movement of at least a first and a second movable component of the medical device from an operable state with regard to a support device, the latching and control unit comprising:
- a drive train biased in a distant position with regard to the support device, wherein the drive train comprises a case and a latching means for latching a first movable component and being movable within the case between an extended and an retracted position and being biased in its latching position, wherein the case is movable between an unstressed and a stressed position with regard to the support device and biased into the unstressed position, wherein the elastic force for biasing the latching means is greater than the elastic force for biasing the case,
- a detection or switch device for detecting a stressed position of the case, coupling means for coupling of at least a partial movement of the second movable component with the movement of the case, and
- a control device which is functionally connected to the detection device which comprises a function for determining a stressed position of the drive train so that the control device determines the movement of the latching means in its retracted position by interaction with the first component and the movement of the drive train in its stressed position by interaction with the second component.

According to an example of the invention, the control device comprises a function which detects the movement of the drive train in its stressed position caused by a movement of the first or the second movable component as activating condition and which in this case puts corresponding second or first component in an operable state. This embodiment of the invention can in particular be related to the design of an electronically controlled mechanism suitable for use within an electro-mechanical medical device for injecting medicament. In this regard, following the insertion of a medicament cartridge into said medical device, it is required that a door mechanism is closed and latched to retain the cartridge. Said door can also serve as the cartridge holder, also requiring closing and latching. The latching and control unit according to the invention allows tracking the status of a medical device. This includes awareness of cartridge presence within the medical device and/or door state (open or closed).

'Cartridge presence' may either refer to whether a cartridge has been inserted onto the medical device or not, or alternatively it may refer to whether the correct cartridge has been inserted or not, as part of a dedicated cartridge package.

The electronically operated mechanism can in particular be realized by an embodiment of the medical device comprising a door and latch system having the latching and control unit, wherein the door and the latch system are physically separated from the floating drive train and an independent latch detection and biasing spring are provided.

According to an example of the invention, the first movable component is a cover which is linked to a housing of the medical device such that, by closing the cover starting from an opened state or by opening the cover starting from a closed state, the cover interacts with the latching means, so that the latching means is moved in its retracted position and the case in a stressed position which is detected by the switch device.

According to a further example of the invention, the first movable component is a cartridge or a cartridge holder which is to be inserted in a housing of the medical device such that, by inserting the cartridge or the cartridge holder into the housing, the cartridge or the cartridge holder interacts with the latching means, so that the latching means is moved in its retracted position and the case in a stressed position which is detected by the detection device.

The second movable component can be an actuation means a part of which interacts with the coupling means of the case such that a predefined movement of the actuation means causes a movement of the case into its stressed position, whereby the detection device detects a trigger position of the actuation means.

In this regard, the actuation means can be an enabling means for enabling the medical device for infusion of a medicament or removal of a substance of the human body.

According to an example of the invention, the actuation means is the drive means. In this regard, the trigger state of the drive means can particularly be the state in which the drive means is not operable, wherein the detection device is coupled to the drive means such that the detection device detects the trigger state of the drive means. The medical device can be designed such that the drive means or the piston rod is positioned outside its operable range by the motor after having reached its fully deployed position and wherein the trigger state of the piston rod is a position outside its operable state.

According to an example of the invention, the medical device can be designed such that the operable range of the drive means is defined by an initial position and a fully deployed position of the drive means between the drive means is moveable, wherein the drive means is moved by the motor from its fully deployed position in an activating position which lies from there beyond the initial position, wherein by moving from the initial position to the activating position the case is moved in its stressed position which is detected by the detection or switch device.

According to an example of the invention, the drive means is a piston rod which can be moved from an initial position into a position in which a distal end of the piston rod contacts the bung of a cartridge inserted into the medical device, and wherein the trigger state of the piston rod is the position in which the distal end of the piston rod contacts the bung of the cartridge.

Generally, the drive means or the piston rod is electro-mechanically driven. In this regard, the control device can be designed such that the operational state of the drive means or the movement of the piston rod is controlled by the control device.

According to another example of the invention, the latching and control unit further comprises a locking and unlocking device for locking the latching means within the case in its extended position, wherein the locking and unlocking device is functionally coupled with the detection device such that the locking and unlocking device is in its locking position when the detection device has detected the movement of the latching means in its retracted position by interaction with the first component and the movement of the drive train in its stressed position by interaction with the second component.

The medical device can generally be a medication delivery device, in particular in the form of an injector-type device, or an apparatus for removal of liquid or tissue from a human body. Further, the medical device can comprise a needle.

According to another aspect of the invention, the use of a medication delivery device according to the invention is provided which is designed for dispensing a medicinal product. The medication delivery device can also be designed for dispensing a pharmaceutical formulation comprising an active compound selected from the group consisting of insulin, growth hormone, low molecular weight heparin, their analogues, and their derivatives.

According to another aspect of the invention, the method of manufacturing or assembling a medication delivery device according to the invention is provided. One aspect of the present invention provides a medication delivery device according to instant invention for dispensing a medicinal product preferably for dispensing a pharmaceutical formulation (e.g. solution, suspension etc.) comprising an active compound selected from the group consisting of insulin, growth hormone, low molecular weight heparin, their analogues and their derivatives.

The term "medical device" and in particular medical delivery devices or "drug delivery devices" according to instant invention shall mean a single-dose or multi-dose or pre-set dose or pre-defined dose, disposable or re-useable device designed to dispense a user selectable or pre-defined dose of a medicinal product, preferably multiple pre-defined doses, e.g. insulin, growth hormones, low molecular weight heparins, and their analogues and/or derivatives etc. Further, the term "medical device" comprises devices or apparatuses for removal of tissue or liquid from a human body. Said device may be of any shape, e.g. compact or pen-type. The medication delivery device can be a pen-type device or an injector-type device. Further, the medication delivery device can comprise a needle.

Additionally, said device may contain components designed to monitor physiological properties such as blood glucose levels, etc. Furthermore, the said device may comprise a needle or may be needle-free. In addition, the said device may comprise a fixed needle or a replaceable needle or a moving needle or a shielded moving needle.

In particular, the term "drug delivery device" shall mean a disposable needle-based pen-type device providing multiple pre-defined doses having mechanical and manual dose delivery and dose selection mechanisms, which is designed for use by persons without formal medical training such as patients. Preferably, the drug delivery device is of the injector-type.

The medical delivery device comprises a drive means or a drive mechanism having drive means for dispensing a set of a dose of a medicament from a medication receptacle of the delivery device in a distal direction. Dose selection or dose setting for selection or for setting a dose of a liquid or non-liquid medicament in a receptacle may be provided through a dosing mechanism or dose setting means or a dose setting mechanism so that the medical delivery device can further comprise a dose selection mechanism or dose setting mechanism for selection or setting the dose of a liquid medicament in the receptacle to be dispensed by the drive mechanism. The dosing mechanism can partly or totally be realized with components or functions of the drive mechanism or can be realized as a separate mechanism.

The term "distal end" according to instant invention shall mean the end of the device or a component of the device which is closest to the dispensing end of the device. The term "proximal end" according to instant invention shall mean the end of the device or a component of the device which is furthest away from the dispensing end of the device.

Accordingly, the "distal direction" is the direction which is directed from the proximal end to the distal end of the device or a component of the device and the "proximal direction" is the direction which is directed from the distal end to the proximal end of the device or a component of the device.

The term "medication receptacle" in the context of the present invention includes a cartridge or receptacle containing the medication as well as a cartridge holder for receiving a cartridge containing the medication. Furthermore, the terms "receptacle" and "cartridge" are exchangeable. This means that by using the term "receptacle", any meaning of the term "cartridge" is included, and vice versa.

The term "receptacle holder" or "cartridge holder" according to instant invention shall mean any component and/or components designed to house a medicament cartridge containing a medication to be delivered by the medication delivery device. Said cartridge holder may be of any shape, e.g. cylindrical or tubular. In general, the cartridge holder may be unitary or a multipart component of a cylindrical tubular or non-tubular shape. It may be made of any suitable material known by a person skilled in the art. Further the cartridge holder is preferably provided with engaging means, e.g. helical threads or part threads or bayonet or the like, on an external and/or internal surface of the distal end and/or proximal end of the cartridge holder designed for engagement with corresponding engaging means located on an exterior and/or interior surface of a housing and/or needle assembly. In a preferred embodiment the cartridge holder is of a unitary tubular design having a part thread located at its proximal end.

Dose delivery may be provided through a mechanical (optionally manual) drive mechanism or drive means or electrical drive mechanism or electro-mechanical mechanism or stored energy drive mechanism, such as a spring, etc. The drive mechanism can in particular comprise a piston being movable in the medication receptacle for displacing the medicament in the receptacle. At the piston a piston rod may be attached, wherein the piston rod is driven by further components of the drive mechanism. The term "piston rod" according to instant invention shall mean a component adapted to operate through/within the housing, designed to translate axial movement (preferably towards the distal end) through/within the medication delivery device, preferably from the drive sleeve to the piston of the cartridge, for the purpose of discharging/dispensing a medication from the cartridge, preferably an injectable product. Said piston rod may be flexible or not. It may be a simple rod, a lead-screw, a rack and pinion system, piston rod, a worm gear system, or the like. The "piston rod" shall further mean a component having a circular or non-circular cross-section. It may be made of any suitable material known by a person skilled in the art.

For example, the piston rod may be driven by a "drive sleeve". The term "drive sleeve" according to instant invention shall preferably mean any essentially tubular component of essentially circular cross-section. According to a preferred embodiment of the present invention, the drive sleeve is a component for driving the piston rod in a distal direction for medication delivery. In a preferred embodiment the drive sleeve is engaged with the piston rod. Preferably the drive sleeve comprises an internal thread for engaging an external thread of the piston rod. The drive sleeve is further preferably releasably connected to the dose dial sleeve, most preferably by a clutch means.

The term "dosing mechanism" according to instant invention shall mean any component and/or components and/or assembly designed to allow a user to select and/or set a dose to be dispensed and/or to provide a force necessary to dispense a dose of a medication. Said dosing mechanism can be designed as manual mechanism or electro-mechanical mechanism or electronic mechanism and may be composed of mechanical and/or electro-mechanical and/or electronic components. Additionally, the dosing mechanism may be engaged with the device housing or may be an independent assembly. For example, the dose setting can be realized by a dose dial sleeve as part of the dosing mechanism.

The dosing mechanism may be operated by an "operating mechanism" or an "operating device". The term "operating mechanism" or "operating device" according to instant invention shall mean any module or any component or set of components designed to be operated by the user in order to control the drive mechanism. When controlling the drive mechanism, force it transmitted to the drive mechanism. The force can be generated manually or by means of a motor. In a preferred embodiment, the operating device comprises actuating keys. In another preferred embodiment, the operating device comprises a dose dosing sleeve or dose dial sleeve. In order to set of dose or to administer the dose of a medicament, the user actuates the medicament delivery device by means of the operating device. For example, if a user wishes to deliver or expel a medicament from the cartridge, the "operating mechanism" is to be actuated and, for example, an operating button or the "operating mechanism is to be pressed which is a component of the operating device. The operating device is functionally coupled with the drive mechanism. The drive mechanism drives a piston, which is movable within the medicament cartridge (not shown) such that the medicament is expelled from the cartridge.

The term "housing" according to instant invention shall preferably mean any exterior housing ("main housing", "body", "shell") or interior housing ("insert", "inner body") having one or more helical threads. The housing may be designed to enable the safe, correct, and comfortable handling of the drug delivery device or any of its mechanism. Usually, it is designed to house, fix, protect, guide, and/or engage with any of the inner components of the drug delivery device (e.g., the drive mechanism, cartridge, plunger, piston rod) by limiting the exposure to contaminants, such as liquid, dust, dirt etc. In general, the housing may be unitary or a multipart component of tubular or non-tubular shape. Usually, the exterior housing serves to house a cartridge, which may be replaceable or non-replaceable, from which a number of doses of a medicinal product may by dispensed. In a more specific embodiment of instant invention, the housing is provided with a plurality of maximum dose stops adapted to be abutted by a radial and/or axial stop provided on the activation means.

The actuation means according to the invention can for example be a part of the drive mechanism and in particular a driving means or a piston rod. The actuation means according to the invention can be used for various mechanisms of various embodiments of medical devices and generally for bringing a component thereof in a stable holding state for maintaining a holding or guiding state of a member of a mechanism or for activating a function of the delivery device. By interaction of the actuation means with this component, this component is brought into and held in a predetermined state so that this component is part of a dynamic process within the medication delivery device.

This dynamic process (e.g. the medication delivery, the setting of a dose, the adjustment of a working mode or the activation of a function of a module of the delivery device like the dosing mechanism) can then be performed. According to the invention, the release of the component by the actuation means, de-activates the component and thus de-activates the before-mentioned dynamic process or the function. For example, the component when engaged and stabilized by means of the actuation means can hold any dynamic member like the piston rod or any mechanism like the dosing mechanism in an operational state and by release of the holding means by the actuation means the dynamic member or the mechanism is not operable in its predetermined function.

In general, the actuation means is an enabling means for enabling the medical device for infusion of a medicament or removal of a substance of the human body. The enabling means can be a mechanical detection which can be operated by a user, for example to activate a function of the medical device. The function can be a function for enabling the medical device for infusion of a medicament or removal of a substance of a human body by a drive means.

In a preferred embodiment of the invention, the component is a cover and in particular a cover of a cartridge holder.

The term "cartridge holder" according to instant invention shall mean any component and/or components designed to house a medicament cartridge containing a medication to be delivered by the medication delivery device. Said cartridge holder may be of any shape, e.g. cylindrical or tubular. In general, the cartridge holder may be unitary or a multipart component of a cylindrical tubular or non-tubular shape. It may be made of any suitable material known by a person skilled in the art. Further the cartridge holder is preferably provided with engaging means, e.g. helical threads or part threads or bayonet or the like, on an external and/or internal surface of the distal end and/or proximal end of the cartridge holder designed for engagement with corresponding engaging means located on an exterior and/or interior surface of a housing and/or needle assembly. In a preferred embodiment the cartridge holder is of a unitary tubular design having a part thread located at its proximal end.

Generally, for the delivery device and/or components or mechanisms thereof an axial or longitudinal direction and a radial direction can be defined. The axial direction corresponds to the longitudinal direction of the delivery device extending in the distal direction of the delivery device.

The term "engaged" according to instant invention shall particularly mean the interlocking of two or more components of the drive mechanism/drug delivery device, e.g. a spline, thread, or meshed teeth connection, preferably the interlocking of helical threads of components ("threadedly engaged").

The term "disengaged" according to instant shall mean the unlocking of two or more components of the dosing mechanism/medication delivery device. Preferably, the term "disengaging" according to instant invention shall mean the unlocking of two or more components of the dosing mechanism/medication delivery device under the force of a biasing means.

The term "coupled" according to instant invention shall mean the connection of two or more components of the drive mechanism/drug delivery device, e.g. using a flange or the like, in which the degree of freedom of the components with respect to each other is limited. In a preferred embodiment one component is permitted to rotate around one axis with respect to another component and is limited from all other rotational and/or translational movement with respect to another component. In a more particular embodiment of instant invention, the drive sleeve is provided with a flange that is coupled to the activation means such that relative rotation about the main longitudinal axis of the drug delivery device is permitted but all other relative movement is essentially prevented.

The term "biasing means" according to instant invention shall preferably mean any component that provides a force on a component and/or components to ensure that the component and/or components are forced together into engagement or forced apart out of engagement. Preferably the biasing means may be manufactured from any suitable flexible force storage material known by a person skilled in the art and may take any suitable form, e.g., a spring.

The invention concerns the use of a medical device according to any of the embodiments described above. The use of the medication delivery device can be provided for dispensing a pharmaceutical formulation comprising an active compound selected from the group consisting of insulin, growth hormone, low molecular weight heparin, their analogues, and their derivatives.

According to the invention, a method of manufacturing or assembling of a medical device according to any of the embodiments described above.

In the following figures a partially sectional view of an embodiment of the latching and control unit according to the invention is shown in different operational states, wherein the latching and control unit is provided for being integrated in a medical delivery device including a housing and a cartridge holder, the latching and control unit comprising a drive train which comprises a case, a detection device and a latching means movably disposed in the case between an extended and a retracted position, wherein the case is biased against a support means of the housing of the deliver device and moveable between a forward and a backward position.

According to the invention, a latching and control unit 1 is provided for being integrated in an apparatus for expelling a medicament from a receptacle of the apparatus or for removal of a liquid or a body tissue from a human body. The latching and control unit 1 is provided for generally latching and unlatching a first movable member or component of a medical apparatus in dependency of the position of a coupling means being coupled to an actuation means of the apparatus.

In particular, the actuation means is a drive means for expelling a medicament from the receptacle of the apparatus or for removal of a liquid or a body tissue from a human body. The receptacle can particularly be realized as cartridge 3, wherein the apparatus further comprises a cartridge holder 5 for receiving the cartridge 3. In the embodiment shown in the figures, the cartridge holder 5 comprises a cover 7 which is pivotally linked to a base structure (not shown) of the cartridge holder 5.

According to an aspect of the invention, the apparatus is a medical delivery device for injecting a medicament from the cartridge.

The latching and control unit 1 according to the invention comprises a drive train 10 which comprises a case 13, a detection device or switch device 15 and a latching means 17 for latching a first movable component movably disposed in the case 13 between an extended or latching and a retracted or unlatching position. In the embodiment of the latching and control unit 1 shown in the figures, the extended position of the latching means 17 is a distal position thereof and the retracted position of the latching means 17 is a proximal position thereof. In general however, the extended position of the latching means 17 can alternatively be a distal position and the retracted position of the latching means 17 a proximal position. The case 13 is biased against a support means 20 of a housing of the delivery device and moveable between a forward and a backward position.

The drive train 10 also comprises a coupling means 13.6 for coupling of at least a partial movement of a second movable component with the movement of the case 13. The coupling means 13.6 can in particular be a locating surface as shown in the figures. The detection device 15 is generally designed for detection of at least a stressed position of the drive train 10. A control device is functionally connected to the detection device 15 and comprises a function for determining at least a stressed position of the drive train and, optionally, an unstressed position of the drive train. Therefore, the control device also determines the movement of the latching means 17 in its retracted position by interaction with the first component and the movement of the drive train 10 in its stressed position by interaction with the second component. In one embodiment of the detection device, the same can comprise a sensor, for example a proximity sensor, for at least a stressed position of the drive train. In the embodiment shown in the figures, the detection device 16 is designed as switching device and comprises a movable part 16 which is movable between a first and a second position or a first and a second switching position. In the embodiment of the latching and control unit 1 shown in the figures, the first position is an extended position of the movable part 16 with regard to the case 13 of the drive train 10 and the second position is a retracted position of the movable part 16 with regard to the case 13 of the drive train 10.

The latching means 17 is biased by a biasing means 18 in an extended position. The latching means 17 comprises a main part 17.1 and a detent 17.2 which protrudes from the main part 17.1. The main part 17.1 is movably disposed within the case 13. The case 13 comprises inner side walls 13.1, 13.2 lying opposed to one another so that they are facing each other. Thereby the inner side walls 13.1, 13.2 are forming a guiding device 14. Further, the case 13 comprises an opening 13.3 through which the detent 17.2 protrudes in order to for a latching element with regard to the receptacle or the cartridge holder 5 or a cover 7 of the cartridge holder 5 or generally a component of a medical apparatus. The case 13 can also comprise coupling means 13.6 by which the case 13 can be moved between a forward and a backward position. The coupling means 13.6 can be a protrusion or a mechanical coupling, for example being formed as part of the case 13.

In the embodiment of the invention shown in the figures, the detent 17.2 is designed for interacting with the cover 7 of the cartridge holder 5. In this regard, the cover 7 comprises a recess 7.1. The cover 7 and the latching and control unit 1 are designed such that a forward part of the detent 17.2 can be positioned in the recess 7.1 for latching the cover 7 in its closing position. The case 13 further comprises a bottom wall 13.4 which is lying opposed to the opening 13.3 with regard to the inner space of the case 13. Between the bottom wall 13.4 and an end portion 17.3 of the main part 17.1 a biasing means 18 is disposed. The biasing means 18 can particularly be a helical spring. The biasing means 18 is designed such that the latching means 17 is moved form the bottom wall 13.4 away so that the detent 17.2 is pushed in an extended position, in which the detent 17.2 protrudes out of the case 13 and is positioned in a forward position with regard to the cover 7.

Further, between the support means 20 of the apparatus or the medical device and an outer wall 13.5 of the casing 13 of the drive train 10 a further biasing means 19 is disposed. The further biasing means 19 is in particular disposed at a forward wall of the support means 20. The casing 13 of the drive train 10 is biased by the biasing means 19 in a forward position, this means into the direction to the movable component or the cover 7. Therefore, the support means 20 is positioned backward or in a proximal direction with regard to the case 13 and in particular with regard to the bottom wall 13.4. Consequently, the biasing means 18 which is disposed between the bottom wall 13.4 and an end portion 17.3 of the main part 17.1 and the biasing means 19 which is disposed between the support means 20 and the outer wall 13.5 of the casing 13 each generate a biasing force which are directed such that they have a component in the same direction which runs along or in a longitudinal direction X1 or in the moving direction of the drive means or generally an actuation means of the medical apparatus or medical device. In the embodiments shown in the figures, the biasing means 18, 19 are positioned one behind the other with regard to the longitudinal direction X1 and both are directed in the longitudinal direction X1.

Figure 1:
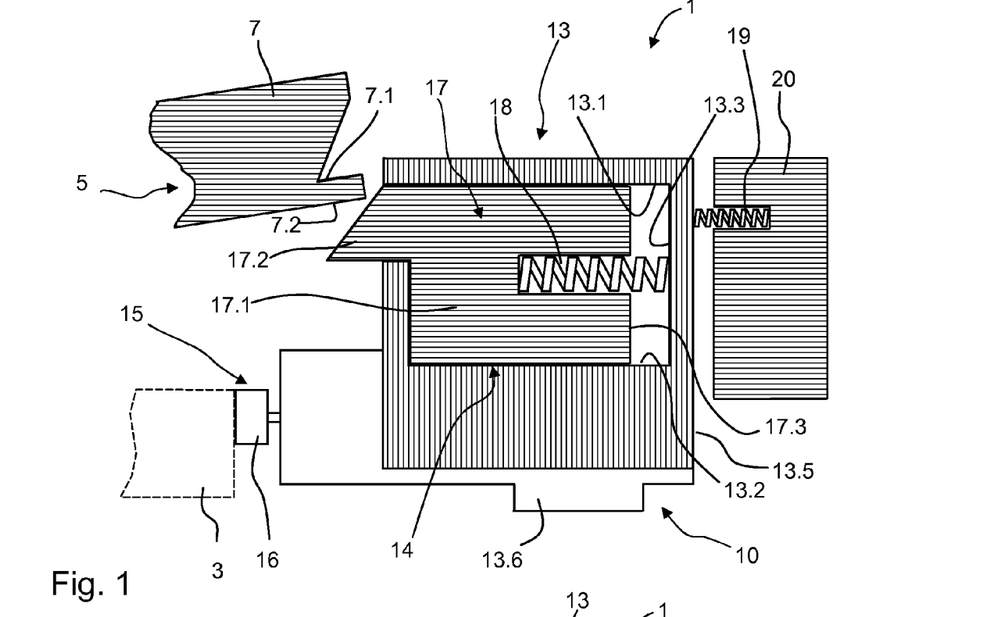
FIG. 1 shows a first state of the latching and control unit when the cover of a recess for receiving a cartridge or a cartridge holder is moved from an open position to a closed position, wherein the cover is in a first opened position in which the case of the drive train is in an unstressed position or in a most forward position with regard to support means and in which the latching means is in an extended position with regard to the case of the drive train.
Figure 4:
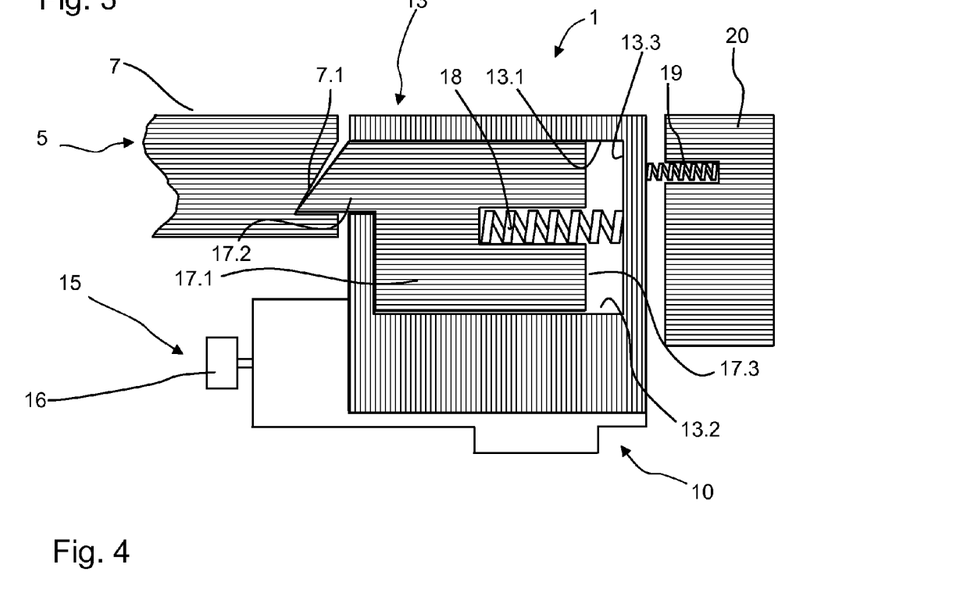
FIG. 4 shows a fourth state of the Latching and control unit when the cover of the cartridge holder is in its closed position, in which the drive train is in the most unstressed or forward position with regard to the support means and in which the latching means is in an extended position with regard to the case of the drive train.
Figure 5:
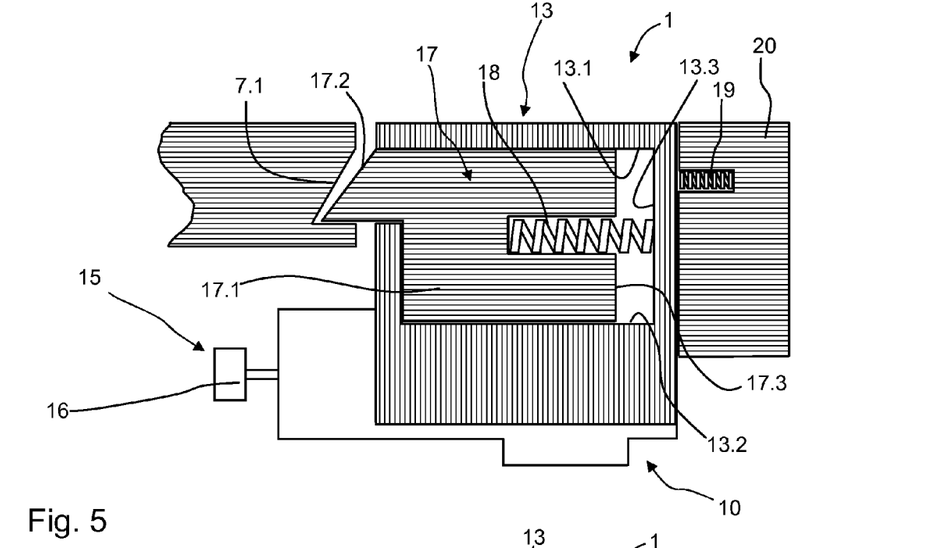
FIG. 5 shows a fifth state of the latching and control unit during its unlatching process, wherein the cover of the cartridge holder is latched by the latching and control unit, the drive train is moved to its most stressed or backward position with regard to the support means by a drive means of the delivery device and the latching means is in an extended position with regard to the case of the drive train.
Figure 6:
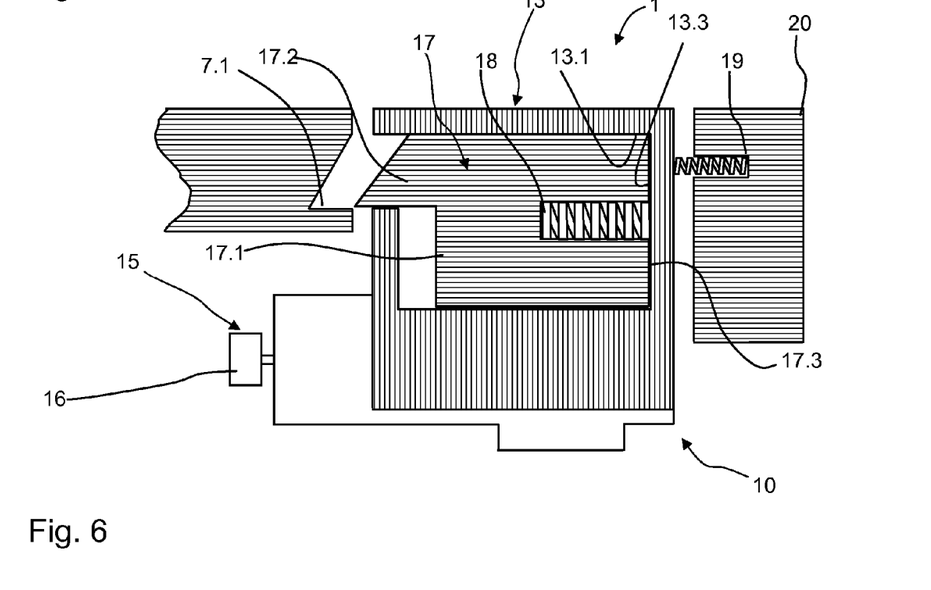
FIG. 6 shows a sixth state of the latching and control unit during its unlatching process, wherein the cover of the cartridge holder is unlatched by the latching and control unit, the drive train is moved in a forward position with regard to the support means by a drive means of the delivery device and the latching means is in a retracted position with regard to the case of the drive train.

The moveable part 16 is particularly biased in its extended or first position. Therefore, the moveable part 16 can be moved in its retracted position by moving the case 13 of the drive train 10 is in a rearward position with regard to the support means 20 when the case 13 of the drive train 10 is in its forward position with regard to the support device 20 (FIGS. 1, 4, 6). This is the case when the cover is in an opened state in which the case 13 is not pressed by the cover 7 in its backward position or when the cover is in a closed state (FIG. 5) and the case 13 is moved in its backward position by the drive means.

The latching and control unit 1 further comprises a locking and unlocking device (not shown in the figures) to which the moveable part 16 of the detection device 15 is connected. The locking and unlocking device is designed such that the locking and unlocking device is put in a locking state when the moveable part 16 is positioned in its second or retracted position. Further, the locking and unlocking device is designed such that the locking and unlocking device is put in a unlocking or opening state when the moveable part 16 is positioned in its first or extended position. Generally, the moveable part is an actuation means, the retracted position of the moveable part 16 is an activating position for locking the locking and unlocking device and the extended position of the moveable part 16 is a releasing or de-activating position of the locking and unlocking device.

Figure 2:
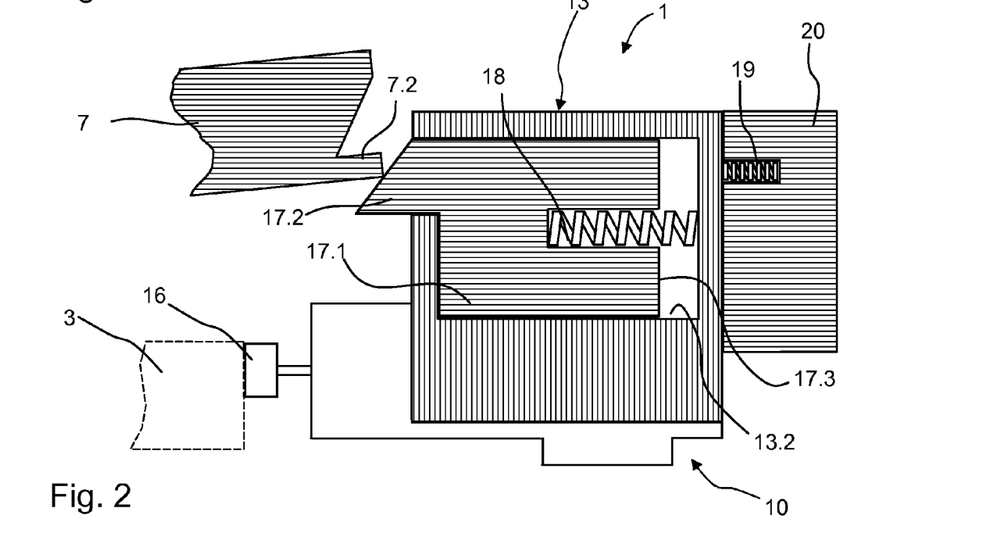
FIG. 2 shows a second state of the latching and control unit when the cover of the cartridge holder is moved from an open position to a closed position, wherein the cover is in a second opened position in which the cover actuates the latching means so that the case of the drive train is in a most backward position with regard to the support means and in which the latching means is in an extended position with regard to the case of the drive train.
Figure 3:
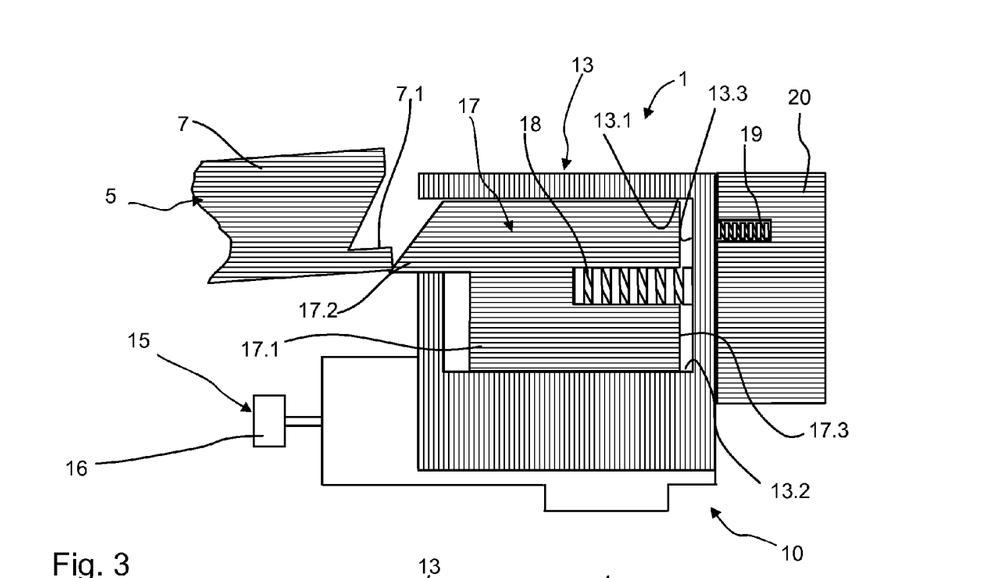
FIG. 3 shows a third state of the latching and control unit when the cover of the cartridge holder is moved from an open position to a closed position, wherein the cover is in a third opened position in which the cover further actuates the latching means so that the case of the drive train is in the most backward or stressed position with regard to the support means and in which the latching means is in an intermediate or a less extended position with regard to the case of the drive train.

In the following, the operation of the latching and control unit 1 according to the invention is described with reference to the figures:

When the cover 7 of the cartridge holder 5 is moved from an open position (FIG. 1) to a closed position (FIG. 4), first an edge 7.2 of protruding part of the cover 7 moves the case 13 of the drive train 10 from a most forward position with regard to the support means 20 into a position in which the case 3 is pressed against the support device 20 (FIG. 2). In this position the locking and unlocking device is put in an unlocking state by the detecting device. This enables, in a second stage of the movement of the cover 7, the latching means 17 to be moved in a retracted position by the cover 7 (FIGS. 2 and 3). In the fully closed position of the cover 7, the detent 17.2 moves into the recess 7.1 so that the moveable part 16 is in its de-activating or retracted position (FIG. 4), so that the latching means 17 is locked with regard to the case 13.

Figure 7:
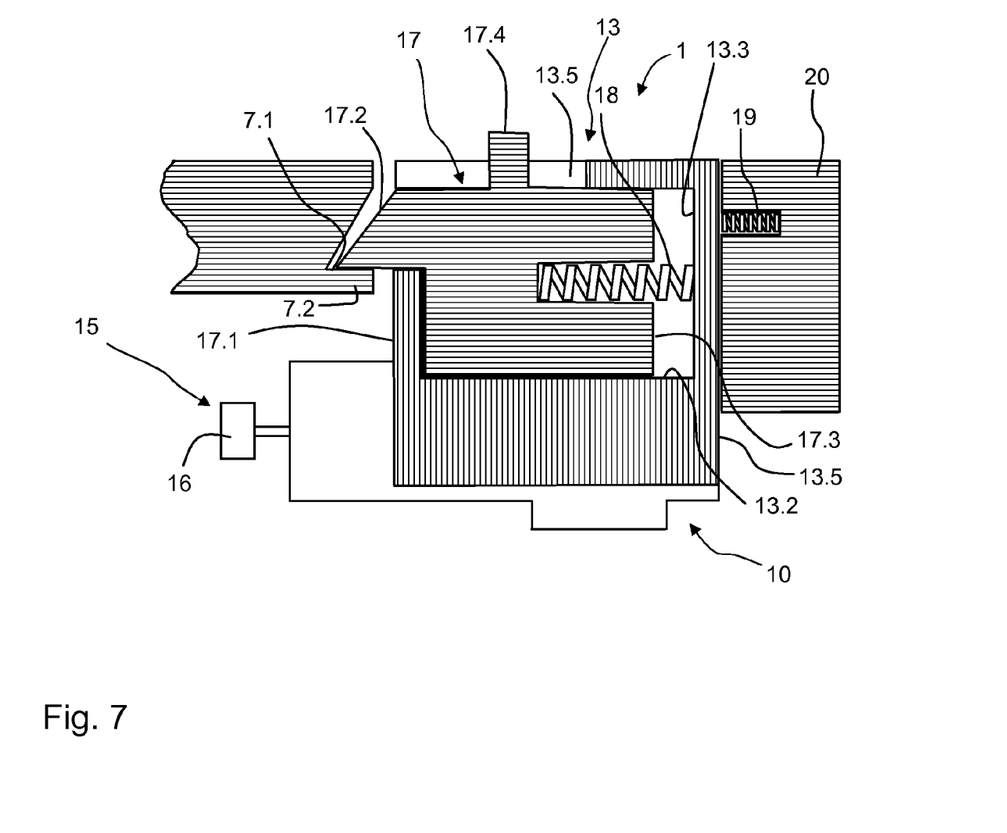
FIG. 7 shows a further embodiment of the latching and control unit in a state as shown in FIG. 5.

For unlocking and opening the cover 7, the drive means (not shown) is such that the drive means moves the case into its backward position, thereby bringing the moveable part 16 into its de-activating or unlocking state. In this state the cover 7 can be opened for example manually by a handle or by an operation element (FIG. 7).

In detail, the cover or door closing procedure occurs in the following stages:

FIG. 1 shows the cover or door 7 in an open position. The latching means 17 is positioned towards the distal end of the medical device as a result of a biasing spring positioned at its proximal end. At this stage, the control device 15 or the movable pat 16 functioning as latch switch is in state one.

FIG. 2 shows the cover or door 7 whilst being closed. Contact between the door or cover 7 and the latching means 17 has resulted in a motion of the latching means towards the proximal end of the medical device, against the latch biasing spring or biasing means 18. By the point at which the latching means 17 is in its most proximal position, the switch device or the movable part 16 in form of a switch has changed from state one to state two.

FIG. 4 shows the cover or door 7 in the closed position. The latch biasing spring has caused the latching means 17 to move back towards the distal end of the medical device, engaging with the profile on the proximal end of the door in such a manner that the door is restrained in the closed position. As the latching means returns to the distal end of the medical device, the latch switch changes from state two back to state one. In this regard, a medical device or a latching means is constructed such that the following insertion of a cartridge, a sequence of events occurs: Firstly, the door 7 is manually closed and the movable part or latch switch 16 temporarily changes from state one to two, and back to one. The said change in state of the latch switch 16 from one to two and back to one then activates a sequence of electronically controlled events which follow: The medical device confirms the presence of a cartridge within the device through the use of a second switch. This process initially describes whether a cartridge has been inserted into the medical device or not. It may also confirm whether or not the correct cartridge has been inserted as part of a dedicated cartridge package.

The invention claimed is:

1. Latching and control unit for integration in a medical device for infusion of a medicament or removal of a substance of a human body by a drive means, the latching and control unit being adapted for controlling the movement of at least a first and a second movable component, the latching and control unit comprising:
    a drive train biased in a distant position with regard to the support device, wherein the drive train comprises a case and a latching means for latching a first movable component and being movable within the case between an extended and an retracted position and being biased in its latching position, wherein the case is movable between an unstressed and a stressed position with regard to the support device and biased into the unstressed position, wherein the elastic force for biasing the latching means is greater than the elastic force for biasing the case,
    a detection device for detecting a stressed position of the case,
    coupling means for coupling of at least a partial movement of the second movable component with the movement of the case,
    a control device which is functionally connected to the detection device which comprises a function for determining a stressed position of the drive train so that the control device determines the movement of the latching means in its retracted position by interaction with the first component and the movement of the drive train in its stressed position by interaction with the second component.

2. Latching and control unit according to claim 1, wherein the first movable component is a cover which is linked to a housing of the medical device such that, by closing the cover starting from an opened state or by opening the cover starting from a closed state, the cover interacts with the latching means, so that the latching means is moved in its retracted position and the case in a stressed position which is detected by the detection device.

3. Latching and control unit according to claim 1, wherein the first movable component is a cartridge or a cartridge holder which is to be inserted in a housing of the medical device such that, by inserting the cartridge or the cartridge holder into the housing, the cartridge or the cartridge holder interacts with the latching means, so that the latching means is moved in its retracted position and the case in a stressed position which is detected by the detection device.

4. Latching and control unit according to claim 1, wherein the second movable component is an actuation means a part of which interacts with the coupling means of the case such that a predefined movement of the actuation means causes a movement of the case into its stressed position, whereby the detection device detects a trigger position of the actuation means.

5. Latching and control unit according to claim 4, wherein the actuation means is an enabling means for enabling the medical device for infusion of a medicament or removal of a substance of the human body.

6. Latching and control unit according to claim 4, wherein the actuation means is the drive means.

7. Latching and control unit according to claim 6, wherein the drive means is a piston rod, wherein the piston rod can be moved outside its operable state after having reached its fully deployed position and wherein the trigger state of the piston rod is a position outside its operable state.

8. Latching and control unit according to claim 6, wherein the drive means is a piston rod which can be moved from an initial position into a position in which a distal end of the piston rod contacts the bung of a cartridge inserted into the medical device, and wherein the trigger state of the piston rod is the position in which the distal end of the piston rod contacts the bung of the cartridge.

9. Latching and control unit according to claim 6, wherein the piston rod is electro-mechanically driven.

10. Latching and control unit according to claim 6, wherein the latching and control unit further comprises a locking and unlocking device for locking the latching means within the case in its extended position, wherein the locking and unlocking device is functionally coupled with the detection device such that the locking and unlocking device is in its locking position when the switch device has detected the movement of the latching means in its retracted position by interaction with the first component and the movement of the drive train in its stressed position by interaction with the second component.

11. Latching and control unit according to claim 6, wherein the trigger state of the drive means is the state in which the drive means is not operable, wherein the detection device is coupled to the drive means such that the detection device detects the trigger state of the drive means.

12. Latching and control unit according to claim 11, wherein the operable range of the drive means is defined by an initial position and a fully deployed position of the drive means between which the drive means is moveable, wherein the drive means is moved by the motor from its fully deployed position in an activating position which lies from there beyond the initial position, wherein by moving from the initial position to the activating position the case is moved in its stressed position.

* * * * *

UNITED STATES PATENT AND TRADEMARK OFFICE
CERTIFICATE OF CORRECTION

PATENT NO.        : 8,512,285 B2
APPLICATION NO. : 13/392778
DATED             : August 20, 2013
INVENTOR(S)       : Bruggemann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 26 days.

Signed and Sealed this

Fifteenth Day of September, 2015

Michelle K. Lee
*Director of the United States Patent and Trademark Office*